(12) United States Patent
Zhang

(10) Patent No.: US 12,349,922 B1
(45) Date of Patent: Jul. 8, 2025

(54) TOURNIQUET TIGHTENING MODULATION METHOD BASED ON BLOOD PRESSURE MEASUREMENT AND VIBRATION POINT SENSING, AND TOURNIQUET TIGHTENING MODULATION DEVICE BASED ON BLOOD PRESSURE MEASUREMENT AND VIBRATION POINT SENSING

(71) Applicant: JIALONG DINGYE (TIANJIN) TECHNOLOGY CO., LTD, Tianjin (CN)

(72) Inventor: Xu Zhang, Tianjin (CN)

(73) Assignee: JIALONG DINGYE (TIANJIN) TECHNOLOGY CO., LTD, Tianjin (CN)

( * ) Notice: Subject to any disclaimer, the term of this patent is extended or adjusted under 35 U.S.C. 154(b) by 0 days.

(21) Appl. No.: 18/900,846

(22) Filed: Sep. 29, 2024

(30) Foreign Application Priority Data

Jun. 6, 2024 (CN) .......................... 202410725480.1

(51) Int. Cl.
*A61B 17/132* (2006.01)
*A61B 17/00* (2006.01)
*A61B 17/135* (2006.01)

(52) U.S. Cl.
CPC ...... *A61B 17/1325* (2013.01); *A61B 17/1327* (2013.01); *A61B 17/1355* (2013.01);
(Continued)

(58) Field of Classification Search
CPC ............ A61B 17/1325; A61B 17/1357; A61B 17/1355; A61B 2017/00022; A61B 2017/00477
See application file for complete search history.

(56) References Cited

U.S. PATENT DOCUMENTS

| 2008/0262533 | A1* | 10/2008 | McEwen | ............ | A61B 17/1355 606/202 |
| 2011/0251636 | A1* | 10/2011 | McEwen | .................. | A61B 8/06 606/202 |

(Continued)

*Primary Examiner* — Tan-Uyen T Ho
*Assistant Examiner* — Cherie M Poland
(74) *Attorney, Agent, or Firm* — Li & Cai Intellectual Property Office

(57) ABSTRACT

A tourniquet tightening modulation method based on blood pressure measurement and vibration point sensing and a tourniquet tightening modulation device based on blood pressure measurement and vibration point sensing are provided. The method includes: wearing a tourniquet at a limb base through a loop, performing a first tightening of the tourniquet according to a first predetermined pressure; when a propagation direction of a vibration wave detected is a predetermined direction and a blood pressure of the limb is below a predetermined threshold, performing a second tightening of the tourniquet according to a second predetermined pressure; recording a tightening moment of the second tightening, and, when a difference between a current moment and the tightening moment exceeds a first predetermined duration, loosening the tourniquet to a predetermined subsequent moment according to a third predetermined pressure, and then performing a third tightening of the tourniquet according to the second predetermined pressure.

3 Claims, 5 Drawing Sheets

(52) U.S. Cl.
CPC .............. *A61B 2017/00022* (2013.01); *A61B 2017/00477* (2013.01)

(56) References Cited

U.S. PATENT DOCUMENTS

| | | | |
|---|---|---|---|
| 2020/0360027 A1* | 11/2020 | Marcus | A63B 24/0087 |
| 2021/0259704 A1* | 8/2021 | Barr | A61B 17/1355 |
| 2022/0015770 A1* | 1/2022 | Couture | A61B 34/30 |

* cited by examiner

TOURNIQUET TIGHTENING MODULATION METHOD BASED ON BLOOD PRESSURE MEASUREMENT AND VIBRATION POINT SENSING, AND TOURNIQUET TIGHTENING MODULATION DEVICE BASED ON BLOOD PRESSURE MEASUREMENT AND VIBRATION POINT SENSING

FIELD OF THE DISCLOSURE

The present disclosure relates to the technical field of tourniquets, and more particularly to a tourniquet tightening modulation method based on blood pressure measurement and vibration point sensing and a tourniquet tightening modulation device based on blood pressure measurement and vibration point sensing.

BACKGROUND OF THE DISCLOSURE

One of the main functions of a tourniquet is to apply pressure to a bleeding limb for emergency hemostasis in tense combat scenarios. Currently, manual tightening methods are usually used for binding the tourniquet. However, in some tense combat scenarios, injured personnel may be unable to promptly secure their injured limbs due to the intensity of the confrontation. Additionally, some individuals may not even notice that their limbs are injured and bleeding due to heightened nervous tension. Some personnel, although they bind the wound, forget to relax the bound area, thus leading to prolonged ischemia and necrosis of body tissues. These situations can cause irreversible harm to the person's body. Therefore, developing a tourniquet tightening modulation method based on blood pressure measurement and vibration point sensing and a tourniquet tightening modulation device based on blood pressure measurement and vibration point sensing, which can promptly and effectively bind the injured limb of personnel for hemostasis, to overcome the deficiencies in the related art mentioned above, has become a technical problem urgently needed to be addressed in the industry.

SUMMARY OF THE DISCLOSURE

In response to the aforementioned problems in the prior art, the embodiment of the present disclosure provides a tourniquet tightening modulation method based on blood pressure measurement and vibration point sensing and a tourniquet tightening modulation device based on blood pressure measurement and vibration point sensing.

In a first aspect, the embodiment of the present disclosure provides a tourniquet tightening modulation method based on blood pressure measurement and vibration point sensing, including: wearing a tourniquet at a base of a limb through a loop, and performing a first tightening of the tourniquet according to a first predetermined pressure; when a propagation direction of a vibration wave detected is a predetermined direction and a blood pressure of the limb is below a predetermined threshold, performing a second tightening of the tourniquet according to a second predetermined pressure; recording a tightening moment of the second tightening, and, when a difference between a current moment and the tightening moment exceeds a first predetermined duration, loosening the tourniquet to a predetermined subsequent moment according to a third predetermined pressure, and then performing a third tightening of the tourniquet according to the second predetermined pressure.

Based on the content of the above embodiment, in the tourniquet tightening modulation method based on blood pressure measurement and vibration point sensing provided in the embodiment of the present disclosure, performing the first tightening of the tourniquet according to the first predetermined pressure includes that the first predetermined pressure is any value between 1.5 kPa to 2.6 kPa, and a pressure on the limb is equal to the first predetermined pressure after performing the first tightening of the tourniquet.

Based on the content of the above embodiment, in the tourniquet tightening modulation method based on blood pressure measurement and vibration point sensing provided in the embodiment of the present disclosure, when the propagation direction of the vibration wave detected is the predetermined direction and the blood pressure of the limb is below the predetermined threshold, then performing the second tightening of the tourniquet according to the second predetermined pressure includes:

$$P_2 = \left[\sigma f(at) + \frac{P_1}{P_{10}}\right]P_{c1} + P_1$$

$$\sigma = \begin{cases} \frac{P_{10} - P_1}{P_{10}f(at)}, & a > 0, \sigma > 0 \text{ and } P_2 > P_1 \\ -\frac{P_{10}}{P_1 f(at)}, & a < 0 \end{cases}$$

wherein $P_2$ is the second predetermined pressure; $\sigma$ is a first modulation coefficient; f(at) is an amplitude of the vibration wave; a is the propagation direction of the vibration wave, and when $\alpha > 0$, the propagation direction of the vibration wave is the predetermined direction, and when $\alpha < 0$, the propagation direction of the vibration wave is opposite to the predetermined direction; t is a duration; $P_1$ is the first predetermined pressure; $P_{10}$ is the predetermined threshold; and $P_{c1}$ is a first supplementary pressure difference.

Based on the content of the above embodiment, in the tourniquet tightening modulation method based on blood pressure measurement and vibration point sensing provided in the embodiment of the present disclosure, when the difference between the current moment and the tightening moment exceeds the first predetermined duration, loosening the tourniquet to the predetermined subsequent moment according to the third predetermined pressure, and then performing the third tightening of the tourniquet according to the second predetermined pressure includes:

$$P_3 = P_2 + \delta(t_s - t_d)P_{c2}$$

$$\delta = \begin{cases} \frac{k}{t_d - t_s}, & |t_s - t_d| \geq T_1 \\ 0, & |t_s - t_d| < T_1 \end{cases}$$

$$k = \begin{cases} 1, & |t_d - t_h| < T_2 \\ 0, & |t_d - t_h| \geq T_2 \end{cases}$$

wherein $P_3$ is the third predetermined pressure; is a second modulation coefficient; $P_{c2}$ is a second supplementary pressure difference; $T_1$ is the first predetermined duration; $T_2$ is a second predetermined duration; $t_s$ is the tightening moment; $t_d$ is the current moment; k is a third modulation coefficient; and || denotes an absolute value.

Based on the content of the above embodiment, in the tourniquet tightening modulation method based on blood pressure measurement and vibration point sensing provided in the embodiment of the present disclosure, after performing the third tightening of the tourniquet according to the second predetermined pressure further includes, when the tourniquet is unable to be tightened any further, pulling a main strap and using a buckle to fix the tourniquet, twisting a windlass rod to increase the pressure of the tourniquet on the limb, and recording a twisting moment.

Based on the content of the above embodiment, in the tourniquet tightening modulation method based on blood pressure measurement and vibration point sensing provided in the embodiment of the present disclosure, after twisting the windlass rod to increase the pressure of the tourniquet on the limb further includes, when a difference between the current moment and the twisting moment exceeds the first predetermined duration and the tourniquet is unable to be loosened, loosening the windlass rod and releasing the toothed triple buckle for a predetermined subsequent duration, then pulling the main strap again and using the toothed triple buckle to fix the tourniquet, twisting the windlass rod to increase the pressure of the tourniquet on the limb, and recording the twisting moment again.

In a second aspect, the embodiment of the present disclosure provides a tourniquet tightening modulation system based on blood pressure measurement and vibration point sensing, including: a main strap 1, wherein a tightening strap 2 is arranged inside the main strap 1, and the tightening strap 2 is fixedly connected to a double-hole windlass rod 3 on one side of an outside of the main strap 1; a tourniquet retention clip 4 provided on the main strap 1, wherein the tourniquet retention clip 4 includes a C-clip, and an opening of the C-clip is connected via a hook and loop fastener 6; a toothed triple buckle 7 provided on one end of the main strap 1, another end of the main strap 1 passing through a gap of the toothed triple buckle 7; and a controller 5 provided on the main strap 1 for loading a corresponding program to implement the tourniquet tightening modulation method based on blood pressure measurement and vibration point sensing according to any of the aforementioned embodiments of the method.

In a third aspect, the embodiment of the present disclosure provides a tourniquet tightening modulation device based on blood pressure measurement and vibration point sensing, including: a first main module for wearing a tourniquet at a base of a limb through a loop and performing a first tightening of the tourniquet according to a first predetermined pressure; a second main module for performing a second tightening of the tourniquet according to a second predetermined pressure when a propagation direction of a vibration wave detected is a predetermined direction and a blood pressure of the limb is below a predetermined threshold; and a third main module for recording a tightening moment of the second tightening, and when a difference between a current moment and the tightening moment exceeds a first predetermined duration, loosening the tourniquet to a predetermined subsequent moment according to a third predetermined pressure, and then performing a third tightening of the tourniquet according to the second predetermined pressure.

In a fourth aspect, the embodiment of the present disclosure provides an electronic device, including: at least one processor, at least one memory, and a communication interface. The at least one processor, the at least one memory, and the communication interface are communicated with each other, the at least one memory stores program instructions executable by the at least one processor, and the at least one processor modulates the program instructions to perform the tourniquet tightening modulation method based on blood pressure measurement and vibration point sensing according to any of the implementations provided in the first aspect.

In a fifth aspect, the embodiment of the present disclosure provides a non-transitory computer-readable storage medium. The non-transitory computer-readable storage medium stores computer instructions that cause a computer to perform the tourniquet tightening modulation method based on blood pressure measurement and vibration point sensing according to any of the implementations provided in the first aspect.

In the tourniquet tightening modulation method based on blood pressure measurement and vibration point sensing and the tourniquet tightening modulation device based on blood pressure measurement and vibration point sensing provided in the embodiments of the present disclosure, the tourniquet can be tightened according to the predetermined pressure by detecting the propagation direction of the vibration wave as the predetermined direction and the blood pressure of the limb being below the predetermined threshold. When the difference between the current moment and the tightening moment exceeds the first predetermined duration, the tourniquet can be loosened to the predetermined subsequent moment according to the predetermined pressure and then tighten again. Therefore, the injured limb of personnel in tense combat scenarios can be automatically bound and loosened, thereby avoiding irreversible injury to the personnel due to special circumstances, and improving the survival rate of personnel in such scenarios.

BRIEF DESCRIPTION OF THE DRAWINGS

To more clearly illustrate the technical solutions in the embodiment of the present disclosure or the prior art, the following is a brief introduction to the drawings required for the description of the embodiments or the prior art. Obviously, the drawings described below are some embodiments of the present disclosure. For those of ordinary skill in the art, other drawings can also be obtained based on these drawings without creative effort.

DETAILED DESCRIPTION OF THE EXEMPLARY EMBODIMENTS

To make the objectives, technical solutions, and advantages of the embodiments of the present disclosure clearer, the following provides a clear and complete description of the technical solutions in the embodiment of the present disclosure in conjunction with the accompanying drawings. It is evident that the described embodiments are part of the embodiments of the present disclosure, but not all of them. Based on the embodiments of the present disclosure, all other embodiments obtained by those skilled in the art without creative efforts fall within the protection scope of the present disclosure. Additionally, the technical features in the various embodiments or individual embodiments provided by the present disclosure can be arbitrarily combined to form feasible technical solutions. Such combinations are not constrained by the sequence of steps and/or the composition mode of the structures but must be based on the realization by those skilled in the art. When combinations of technical solutions are mutually contradictory or impossible to achieve, it should be considered that such combinations do not exist and are not within the protection scope claimed by the present disclosure. If there are step numbers in the following embodiments, they are set only for the convenience of explanation and do not limit the sequence of the steps. The execution sequence of the steps in the embodiment can be adaptively adjusted based on the understanding of those skilled in the art.

Figure 1:
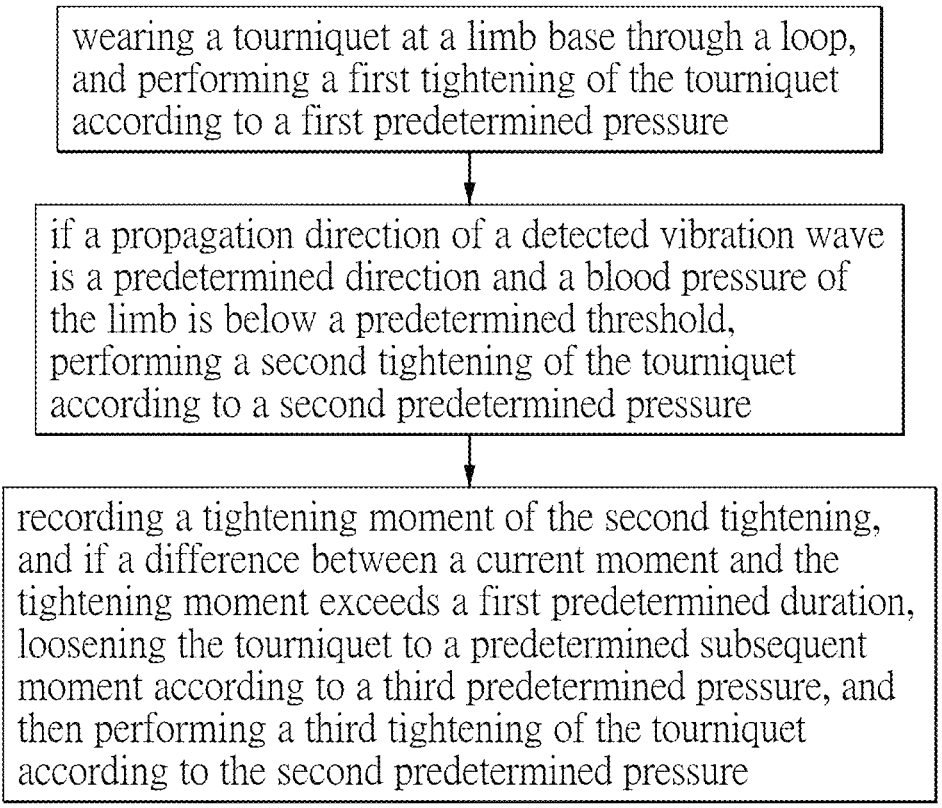
FIG. 1 is a flowchart illustrating a tourniquet tightening modulation method based on blood pressure measurement and vibration point sensing provided in an embodiment of the present disclosure.

The embodiment of the present disclosure provides a tourniquet tightening modulation method based on blood pressure measurement and vibration point sensing. Referring to FIG. 1, the method includes: wearing a tourniquet at a base of a limb through a loop, and performing a first tightening of the tourniquet according to a first predetermined pressure; when a propagation direction of a vibration wave detected is a predetermined direction and a blood pressure of the limb is below a predetermined threshold, performing a second tightening of the tourniquet according to a second predetermined pressure; recording a tightening moment of the second tightening, and when a difference between a current moment and the tightening moment exceeds a first predetermined duration, loosening the tourniquet to a predetermined subsequent moment according to a third predetermined pressure, and then performing a third tightening of the tourniquet according to the second predetermined pressure.

Based on the content of the above embodiment, as an optional embodiment, in the tourniquet tightening modulation method based on blood pressure measurement and vibration point sensing provided in the embodiment of the present disclosure, performing the first tightening of the tourniquet according to the first predetermined pressure includes that the first predetermined pressure is any value between 1.5 kPa to 2.6 kPa, and a pressure on the limb is equal to the first predetermined pressure after performing the first tightening of the tourniquet.

Specifically, the tourniquet is worn at the base of the limb (such as the thigh base or the arm base) through a loop. At this time, the tourniquet is still relatively loose. After performing the first tightening of the tourniquet, the tourniquet can be bound to the limb with a comfortable pressure that the human body can bear (i.e., the first predetermined pressure), ensuring that the tourniquet bound to the limb will not loosen. In another embodiment, the first predetermined pressure can be 1.8 kPa, 2 kPa, 2.2 kPa, or 2.5 kPa.

Based on the content of the above embodiment, as an optional embodiment, in the tourniquet tightening modulation method based on blood pressure measurement and vibration point sensing provided in the embodiment of the present disclosure, when the propagation direction of the vibration wave detected is the predetermined direction and the blood pressure of the limb is below the predetermined threshold, then performing the second tightening of the tourniquet according to the second predetermined pressure includes:

$$P_2 = \left[\sigma f(at) + \frac{P_1}{P_{10}}\right]P_{c1} + P_1$$

$$\sigma = \begin{cases} \frac{P_{10} - P_1}{P_{10}f(at)}, a > 0, \sigma > 0 \text{ and } P_2 > P_1 \\ -\frac{P_{10}}{P_1 f(at)}, a < 0 \end{cases}$$

wherein $P_2$ is the second predetermined pressure; $\sigma$ is a first modulation coefficient; f(at) is an amplitude of the vibration wave; a is the propagation direction of the vibration wave, and when $\alpha>0$, the propagation direction of the vibration wave is the predetermined direction, and when $\alpha<0$, the propagation direction of the vibration wave is opposite to the predetermined direction; t is a duration; $P_1$ is the first predetermined pressure; $P_{10}$ is the predetermined threshold; and $P_{c1}$ is a first supplementary pressure difference.

It should be noted that the values of the second predetermined pressure $P_2$, the first predetermined pressure $P_1$, the predetermined threshold $P_{10}$, and the first supplementary pressure difference $P_{c1}$ can be specifically set according to actual conditions. Any related set values fall within the protection scope of the present disclosure.

Based on the content of the above embodiment, as an optional embodiment, in the tourniquet tightening modulation method based on blood pressure measurement and vibration point sensing provided in the embodiment of the present disclosure, when the difference between the current moment and the tightening moment exceeds the first predetermined duration, loosening the tourniquet to the predetermined subsequent moment according to the third predetermined pressure, and then performing the third tightening of the tourniquet according to the second predetermined pressure includes:

$$P_3 = P_2 + \delta(t_s - t_d)P_{c2}$$

$$\delta = \begin{cases} \frac{k}{t_d - t_s}, |t_s - t_d| \geq T_1 \\ 0, |t_s - t_d| < T_1 \end{cases}$$

$$k = \begin{cases} 1, |t_d - t_h| < T_2 \\ 0, |t_d - t_h| \geq T_2 \end{cases}$$

wherein $P_3$ is the third predetermined pressure; is a second modulation coefficient; $P_{c2}$ is a second supplementary pressure difference; $T_1$ is the first predetermined duration; $T_2$ is a second predetermined duration; $t_s$ is the tightening moment; $t_d$ is the current moment; k is a third modulation coefficient; and ‖ denotes an absolute value.

It should be noted that the third predetermined pressure $P_3$, the second supplementary pressure difference $P_{c2}$, the first predetermined duration $T_1$, the second predetermined duration $T_2$, the tightening moment $t_s$ and the current moment $t_d$ can be specifically set according to actual conditions. Any related set values fall within the protection scope of the present disclosure.

Based on the content of the above embodiment, as an optional embodiment, in the tourniquet tightening modulation method based on blood pressure measurement and vibration point sensing provided in the embodiment of the present disclosure, after performing the third tightening of the tourniquet according to the second predetermined pressure further includes, when the tourniquet is unable to be tightened any further, pulling a main strap and using a toothed triple buckle to fix the tourniquet, twisting a windlass rod to increase the pressure of the tourniquet on the limb, and recording a twisting moment.

Specifically, in tense combat scenarios, there is a risk of a controller being damaged. When the controller is damaged and unable to automatically tighten the tourniquet, the tourniquet can be manually tightened by using the toothed triple buckle to fix the tourniquet and then the windlass rod is twisted to increase the pressure on the limb to achieve hemostasis.

Based on the content of the above embodiment, as an optional embodiment, in the tourniquet tightening modulation method based on blood pressure measurement and vibration point sensing provided in the embodiment of the present disclosure, after twisting the windlass rod to increase the pressure of the tourniquet on the limb further includes, when the difference between the current moment and the twisting moment exceeds the first predetermined duration and the tourniquet is unable to be loosened, loosening the windlass rod and releasing the toothed triple buckle for a predetermined subsequent duration, then pulling the main strap again and using the toothed triple buckle to fix the tourniquet, twisting the windlass rod to increase the pressure of the tourniquet on the limb, and recording the twisting moment again.

Specifically, in the tense combat scenarios, there is a risk of the controller being damaged. When the controller is damaged and unable to automatically loosen the tourniquet, the tourniquet can be manually loosened by loosening the windlass rod to relieve the pressure on the limb and releasing the toothed triple buckle to further loosen the tourniquet, so as to prevent prolonged blood loss and tissue necrosis. After the subsequent predetermined duration, the tourniquet can be manually tightened again using the toothed triple buckle and the windlass rod is twisted to continue applying pressure to the limb for hemostasis.

In the tourniquet tightening modulation method based on blood pressure measurement and vibration point sensing provided in the embodiment of the present disclosure, the tourniquet can be tightened according to the predetermined pressure by detecting the propagation direction of the vibration wave as the predetermined direction and the blood pressure of the limb being below the predetermined threshold. When the difference between the current moment and the tightening moment exceeds the first predetermined duration, the tourniquet can be loosened to the predetermined subsequent moment according to the predetermined pressure and then tighten again. Therefore, the injured limb of personnel in tense combat scenarios can be automatically bound and loosened, thereby avoiding irreversible injury to the personnel due to special circumstances, and improving a survival rate of personnel in such scenarios.

Figure 4:
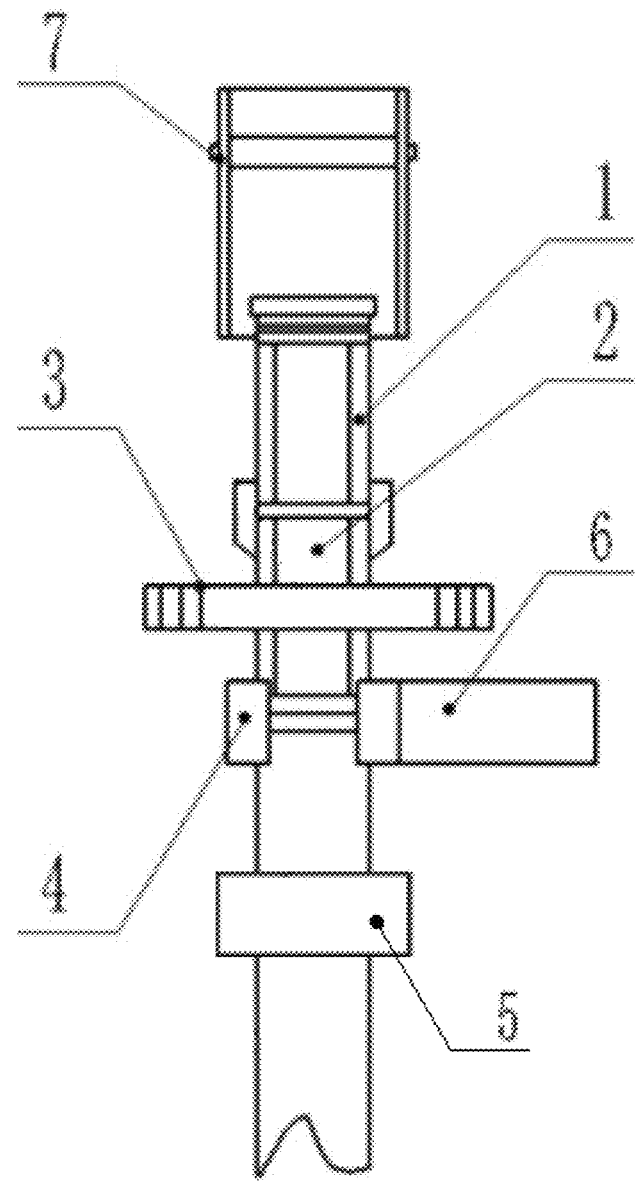
FIG. 4 is a schematic structural diagram of a tourniquet tightening modulation system based on blood pressure measurement and vibration point sensing provided in the embodiment of the present disclosure.

The embodiment of the present disclosure provides a tourniquet tightening modulation system based on blood pressure measurement and vibration point sensing. Referring to FIG. 4, the system includes: a main strap 1, a tightening strap 2 is arranged inside the main strap 1, and the tightening strap 2 fixedly connected to a double-hole windlass rod 3 on one side of an outside of the main strap 1; a tourniquet retention clip 4 provided on the main strap 1, the tourniquet retention clip 4 includes a C-clip, and an opening of the C-clip is connected via a hook and loop fastener 6; a toothed triple buckle 7 provided on one end of the main strap 1, and another end of the main strap 1 passes through a gap of the toothed triple buckle 7; and a controller 5 provided on the main strap 1 for loading a corresponding program to implement the tourniquet tightening modulation method based on blood pressure measurement and vibration point sensing according to any of the aforementioned embodiments. It should be noted that the controller 5 integrates a blood pressure sensor and a vibration wave direction sensor, which are respectively used to sense human blood pressure and the propagation direction of limb vibration waves.

Figure 5:
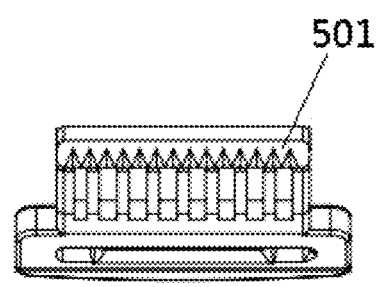
FIG. 5 is a schematic diagram of a locking tooth structure provided in the embodiment of the present disclosure.
Figure 6:
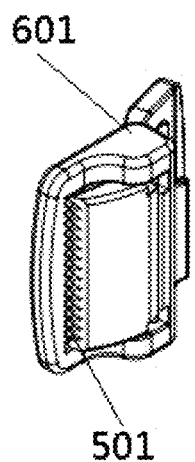
FIG. 6 is a schematic diagram of a toothed buckle structure provided in the embodiment of the present disclosure.
Figures 7A, 7B:
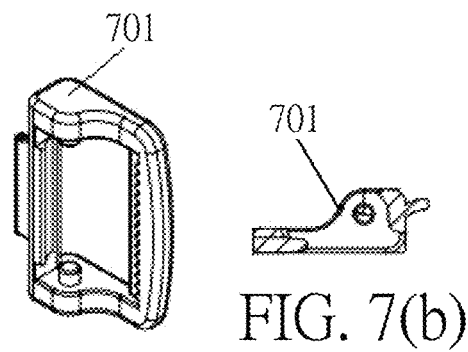
FIG. 7(*a*) and FIG. 7(*b*) are schematic diagrams of a locking plate structure provided in the embodiment of the present disclosure.
Figure 8:
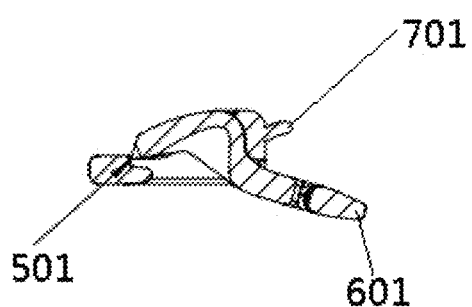
FIG. 8 is a schematic diagram of the combined toothed triple buckle structure provided in the embodiment of the present disclosure.
Figure 9:
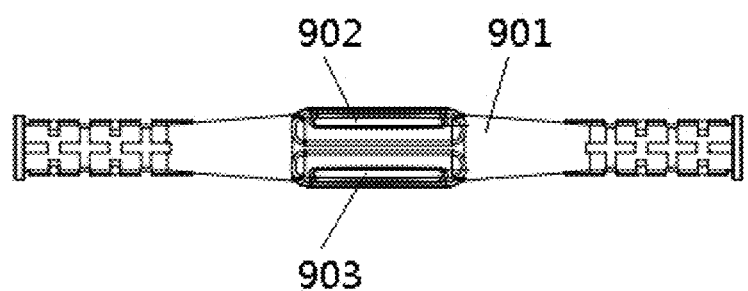
FIG. 9 is a schematic diagram of a double-hole windlass rod structure provided in the embodiment of the present disclosure.

The specific structure of the toothed triple buckle 7 can be seen in FIG. 5 to FIG. 8. FIG. 5 shows a locking tooth 501, which is one of the components of the toothed triple buckle 7, used for fastening the main strap 1. FIG. 6 shows a toothed buckle 601, which is another component of the toothed triple buckle 7, used in combination with the locking tooth 501 to provide a carrier for the locking tooth 501. FIG. 7(a) and FIG. 7(b) show a locking plate 701, which is another component of the toothed triple buckle 7. Specifically, FIG. 7(a) provides a perspective view of the locking plate 701, and FIG. 7(b) provides a side view of the locking plate 701. The locking plate 701 is used to be engaged to the toothed buckle 601 to fasten the main strap 1. The combined structure of the toothed triple buckle is shown in FIG. 8, in which the locking tooth 501 is loaded into the toothed buckle 601, the toothed buckle 601 is engaged to the locking plate 701, and a front edge of the locking plate 701 cooperates with the locking tooth 501 to clamp and fasten the main strap 1. The main strap 1 stretches outward through the toothed triple buckle 7. When a turning point is higher than two force points, the locking tooth 501 will lock the main strap 1. The greater the force is, the tighter the locking tooth 501 will be locked. The double-hole windlass rod 3 can be seen in FIG. 9. The double-hole windlass rod 3 includes a windlass rod 901, a first hole 902, and a second hole 903. In the related technology, the tourniquet windlass rod is of the straight-through type, with a single tightening strap passing through the straight-through windlass rod. The straight-through windlass rod can move freely along the tightening strap, which is not convenient for operating the windlass rod at a fixed position. In contrast, the double-hole windlass rod 3 can basically fix the windlass rod at a predetermined position on the tightening strap, thereby preventing the tightening strap from breaking under prolonged high tension and ensuring even and secure force distribution.

Figure 2:
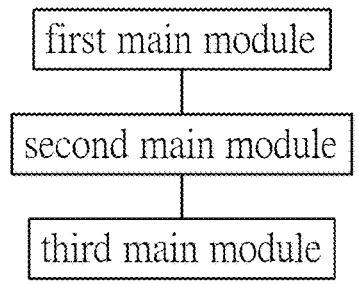
FIG. 2 is a schematic structural diagram of the tourniquet tightening modulation device based on blood pressure measurement and vibration point sensing provided in the embodiment of the present disclosure.

The implementation of the various embodiments of the present disclosure is based on programmatic processing by devices with processor functions. Therefore, in engineering practice, the technical solutions and functions of the various embodiments of the present disclosure can be encapsulated into various modules. Based on the practical situation, on the basis of the above embodiments, one particular embodiment of the present disclosure provides a tourniquet tightening modulation device based on blood pressure measurement and vibration point sensing, which is used to execute the tourniquet tightening modulation method based on blood pressure measurement and vibration point sensing in the aforementioned embodiments. Referring to FIG. 2, the device includes: a first main module for wearing the tourniquet at a base of a limb through a loop and performing a first tightening of the tourniquet according to a first predetermined pressure; a second main module for performing a second tightening of the tourniquet according to a second predetermined pressure when a propagation direction of a vibration wave detected is a predetermined direction and a blood pressure of the limb is below a predetermined threshold; a third main module for recording a tightening moment of a second tightening, and when a difference between a current moment and the tightening moment exceeds a first predetermined duration, loosening the tourniquet to a predetermined subsequent moment according to a third predetermined pressure, and then performing a third tightening of the tourniquet according to the second predetermined pressure.

The tourniquet tightening modulation device based on blood pressure measurement and vibration point sensing provided in the embodiment of the present disclosure utilizes several modules in FIG. 2 to tighten the tourniquet according to the predetermined pressure when the propagation direction of the vibration wave detected is the predetermined direction and the blood pressure of the limb is below the predetermined threshold; and when the difference between the current moment and the tightening moment exceeds the first predetermined duration, the tourniquet is loosened to the predetermined subsequent moment according to the predetermined pressure and tightens again. Therefore, the injured limb of personnel in tense combat scenarios can be automatically bound and loosened, thereby avoiding irreversible injury due to special circumstances and improving the survival rate of personnel in such scenarios.

It should be noted that the device provided by the present disclosure can be used not only to implement the method in the embodiments mentioned above but also to implement the method in other embodiments provided by the present disclosure. The difference lies only in the setting of the corresponding functional modules, and the principle is basically the same as that of the embodiment mentioned above. As long as those skilled in the art, based on the above embodiment, refer to the specific technical solutions in other embodiments, and obtain the corresponding technical means through the combination of technical features, and the technical solutions composed of these technical means ensure the practicality of the technical solution, they can improve the device in the above embodiments to obtain the corresponding device-type embodiments to implement the method in other method-type embodiments.

For example, based on the content of the above embodiment, as an optional embodiment, the tourniquet tightening modulation device based on blood pressure measurement and vibration point sensing provided in the embodiment of the present disclosure further includes the first sub-module for performing the first tightening of the tourniquet according to the first predetermined pressure, wherein the first predetermined pressure is any value between 1.5 kPa to 2.6 kPa, and the pressure on the limb is equal to the first predetermined pressure after performing the first tightening of the tourniquet.

Based on the content of the above embodiment, as an optional embodiment, the tourniquet tightening modulation device based on blood pressure measurement and vibration point sensing provided in the embodiment of the present disclosure further includes the second sub-module for performing the second tightening of the tourniquet according to the second predetermined pressure, and when the propagation direction of the vibration wave detected is the predetermined direction and the blood pressure of the limb is below the predetermined threshold, includes:

$$P_2 = \left[\sigma f(at) + \frac{P_1}{P_{10}}\right] P_{c1} + P_1$$

$$\sigma = \begin{cases} \dfrac{P_{10} - P_1}{P_{10} f(at)}, & a > 0, \sigma > 0 \text{ and } P_2 > P_1 \\ -\dfrac{P_{10}}{P_1 f(at)}, & a < 0 \end{cases}$$

wherein $P_2$ is the second predetermined pressure; $\sigma$ is a first modulation coefficient; $f(at)$ is an amplitude of the vibration wave; $\alpha$ is the propagation direction of the vibration wave, and when $\alpha > 0$, the propagation direction of the vibration wave is the predetermined direction, and when $\alpha < 0$, the propagation direction of the vibration wave is opposite to the predetermined direction; t is a duration; $P_1$ is the first predetermined pressure; $P_{10}$ is the predetermined threshold; and $P_{c1}$ is a first supplementary pressure difference.

Based on the content of the above embodiment, as an optional embodiment, the tourniquet tightening modulation device based on blood pressure measurement and vibration point sensing provided in the embodiment of the present disclosure further includes the third sub-module for performing, when the difference between the current moment and the tightening moment exceeds the first predetermined duration, loosening the tourniquet to the predetermined subsequent moment according to the third predetermined pressure, and then performing the third tightening of the tourniquet according to the second predetermined pressure includes:

$$P_3 = P_2 + \delta(t_s - t_d) P_{c2}$$

$$\delta = \begin{cases} \dfrac{k}{t_d - t_s}, & |t_s - t_d| \geq T_1 \\ 0, & |t_s - t_d| < T_1 \end{cases}$$

$$k = \begin{cases} 1, & |t_d - t_h| < T_2 \\ 0, & |t_d - t_h| \geq T_2 \end{cases}$$

wherein $P_3$ is the third predetermined pressure; $\delta$ is a second modulation coefficient; $P_{c2}$ is a second supplementary pressure difference; $T_1$ is the first predetermined duration; $T_2$ is a second predetermined duration; $t_s$ is the tightening moment; $t_d$ is the current moment; k is a third modulation coefficient; and $\|$ denotes an absolute value.

Based on the content of the above embodiment, as an optional embodiment, the tourniquet tightening modulation device based on blood pressure measurement and vibration point sensing provided in the embodiment of the present disclosure further includes a fourth sub-module for performing, after performing the third tightening of the tourniquet according to the second predetermined pressure, when the tourniquet cannot be tightened any further, pulling a main strap and using a toothed triple buckle to fix the tourniquet, twisting a windlass rod to increase the pressure of the tourniquet on the limb, and recording a twisting moment.

Based on the content of the above embodiment, as an optional embodiment, the tourniquet tightening modulation device based on blood pressure measurement and vibration point sensing provided in the embodiment of the present disclosure further includes a fifth sub-module for performing, after twisting the windlass rod to increase the pressure of the tourniquet on the limb further includes, when the difference between the current moment and the twisting moment exceeds the first predetermined duration and the tourniquet is unable to be loosened, loosening the windlass rod and releasing the toothed triple buckle for a predetermined subsequent duration, then pulling the main strap again and using the toothed triple buckle to fix the tourniquet, twisting the windlass rod to increase the pressure of the tourniquet on the limb, and recording the twisting moment again.

Figure 3:
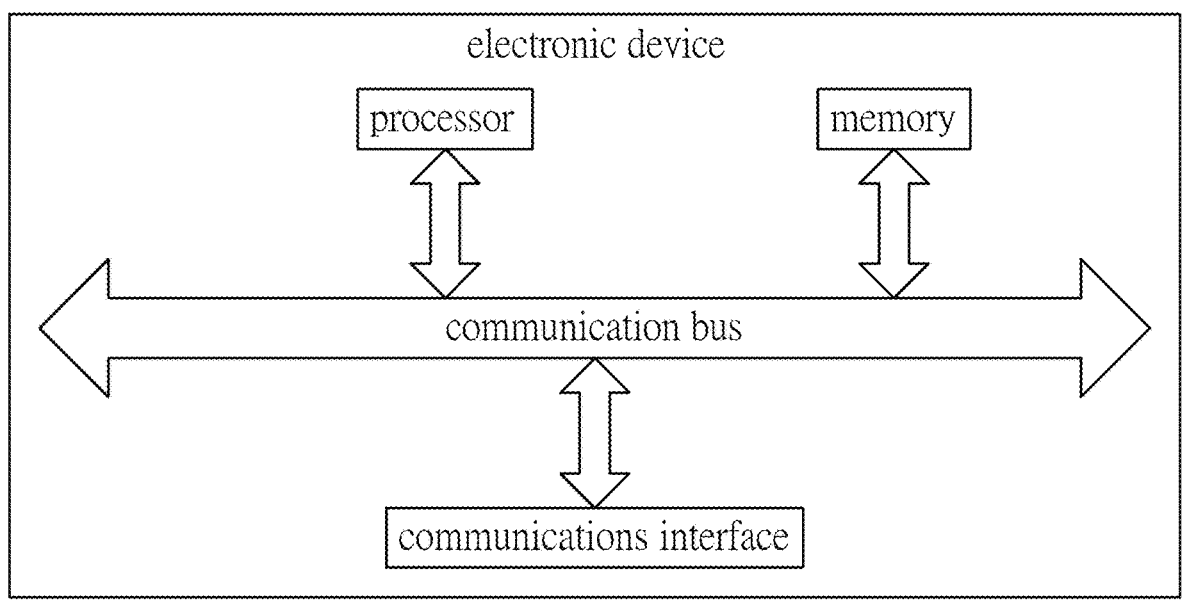
FIG. 3 is a schematic structural diagram of a physical structure of an electronic device provided in the embodiment of the present disclosure.

The method of the embodiment of the present disclosure is implemented relying on an electronic device. Therefore, it is necessary to introduce the related electronic device. For the purpose, one particular embodiment of the present disclosure provides an electronic device, as shown in FIG. 3. The electronic device includes at least one processor, a communication interface, at least one memory, and a communication bus. The at least one processor, the communication interface, and the at least one memory are communicated with each other through the communication bus. The at least one processor can modulate logical instructions in the at least one memory to execute all or part of the steps of the method provided by the various embodiments.

In addition, the logical instructions in the at least one memory mentioned above can be implemented in the form of software function units and can be sold or used as independent products when stored in a computer-readable storage medium. It can be understood that the technical solutions of the present disclosure or the part that contributes to the prior art can be embodied in the form of a software product. The computer software product is stored in a storage medium and includes several instructions to enable a computer device (which can be a personal computer, a server, or a network device, etc.) to execute all or part of the steps of the method described in the various embodiments of the present disclosure. The storage medium mentioned above includes a USB flash drive, a mobile hard drive, a read-only memory (ROM), a random access memory (RAM), a magnetic disk, or an optical disk and other media that can store program codes.

The embodiments described above are merely illustrative. The units described as separate components can be physically separate or not. The components displayed as units can be physical units or not, i.e., they can be located in one place or distributed across multiple network units. It is possible to select some or all modules according to actual needs to achieve the purposes of the present embodiment. Those skilled in the art can understand and implement without creative effort.

Through the description of the above embodiments, those skilled in the art can clearly understand that the various embodiments can be implemented with software plus the necessary general hardware platform, or they can be implemented with hardware. It can be understood that the technical solutions described above or the part that contributes to the prior art can be embodied in the form of the software product. The computer software product can be stored in a computer-readable storage medium such as the ROM/RAM, the magnetic disk, the optical disk, etc., and includes several instructions to enable the computer device (which can be the personal computer, the server, or the network device, etc.) to execute the method described in each embodiment or some parts of each embodiment.

The flowcharts and block diagrams in the figures illustrate the architecture, functionality, and operation of possible implementations of systems, methods, and computer program products according to various embodiments of the present disclosure. In this regard, each block in the flowchart or block diagram can represent a module, a program segment, or a portion of code that includes one or more executable instructions for implementing the specified logical function(s). It should also be noted that, in some alternative implementations, the functions indicated in the blocks may occur out of the order noted in the figures. For example, two blocks shown in succession may be executed substantially concurrently, or sometimes they may be executed in the reverse order, depending upon the functionality involved. It is also to be noted that each block of the block diagrams and/or flowcharts, and combinations of blocks in the block diagrams and/or flowcharts, can be implemented by special-purpose hardware-based systems that perform the specified functions or acts, or by combinations of special-purpose hardware and computer instructions.

It should be understood that the terms "comprise," "include," or any variations thereof are intended to cover a non-exclusive inclusion, such that a process, method, article, or device that includes a list of elements does not include only those elements but may include other elements not expressly listed or inherent to such a process, method, article, or device. Without further limitations, elements defined by the phrase "comprise a . . . " do not exclude the presence of additional identical elements in the process, method, article, or device that includes the elements. Any reference to "predetermined threshold," "preset threshold," or similar expressions without specific values can be determined by those skilled in the art through simple tests or appropriate adjustments to determine specific values.

Finally, it should be noted that the above embodiments are intended to illustrate the technical solutions of the present disclosure and not to limit them. Although the present disclosure has been described in detail with reference to the foregoing embodiments, it should be understood by those skilled in the art that they can still modify the technical solutions described in the foregoing embodiments or make equivalent replacements for some of the technical features. Such modifications or replacements do not depart from the spirit and scope of the technical solutions of the present disclosure.

What is claimed is:

1. A tourniquet tightening modulation system based on blood pressure measurement and vibration point sensing, comprising: a main strap (1), wherein a tightening strap (2) is arranged inside the main strap (1), and the tightening strap (2) is fixedly connected to a double-hole windlass rod (3) on one side of an outside of the main strap (1); a tourniquet retention clip (4) provided on the main strap (1), wherein the tourniquet retention clip (4) includes a C-clip, and an opening of the C-clip is connected via a hook and loop fastener (6); a toothed triple buckle (7) provided on one end of the main strap (1), another end of the main strap (1) passing through a gap of the toothed triple buckle (7); and a controller (5) provided on the main strap (1) for loading a corresponding program to implement: when wearing a tourniquet at a base of a limb through a loop, performing a first tightening of the tourniquet according to a first predetermined pressure; when a propagation direction of a vibration wave detected is a predetermined direction and a blood pressure of the limb is below a predetermined threshold, performing a second tightening of the tourniquet according to a second predetermined pressure; recording a tightening moment of the second tightening, and, when a difference between a current moment and the tightening moment exceeds a first predetermined duration, loosening the tourniquet to a predetermined subsequent moment according to a third predetermined pressure, and then performing a third tightening of the tourniquet according to the second predetermined pressure; wherein performing the first tightening of the tourniquet according to the first predetermined pressure includes that the first predetermined pressure is any value between 1.5 kPa to 2.6 kPa, and a pressure on the limb is equal to the first predetermined pressure after performing the first tightening of the tourniquet; wherein, when the propagation direction of the vibration wave detected is the predetermined direction and the blood pressure of the limb is below the predetermined threshold, then performing the second tightening of the tourniquet according to the second predetermined pressure includes:

$$P_2 = \left[\sigma f(at) + \frac{P_1}{P_{10}}\right] P_{c1} + P_1$$

$$\sigma = \begin{cases} \dfrac{P_{10} - P_1}{P_{10} f(at)}, & a > 0, \sigma > 0 \text{ and } P_2 > P_1 \\ -\dfrac{P_{10}}{P_1 f(at)}, & a < 0 \end{cases}$$

wherein $P_2$ is the second predetermined pressure; $\sigma$ is a first modulation coefficient; f(at) is an amplitude of the vibration wave; $\alpha$ is the propagation direction of the vibration wave, and when $\alpha > 0$, the propagation direction of the vibration wave is the predetermined direction, and when $\alpha < 0$, the propagation direction of the vibration wave is opposite to the predetermined direction; t is a duration; $P_1$ is the first predetermined pressure; $P_{10}$ is the predetermined threshold; and $P_{c1}$ is a first supplementary air pressure difference; wherein, when the difference between the current moment and the tightening moment exceeds the first predetermined duration, loosening the tourniquet to the predetermined subsequent moment according to the third predetermined pressure, and then performing the third tightening of the tourniquet according to the second predetermined pressure includes:

$$P_3 = P_2 + \delta(t_s - t_d) P_{c2}$$

$$\delta = \begin{cases} \dfrac{k}{t_d - t_s}, & |t_s - t_d| \geq T_1 \\ 0, & |t_s - t_d| < T_1 \end{cases}$$

$$k = \begin{cases} 1, & |t_d - t_h| < T_2 \\ 0, & |t_d - t_h| \geq T_2 \end{cases}$$

wherein $P_3$ is the third predetermined pressure; $\sigma$ is a second modulation coefficient; $P_{c2}$ is a second supplementary air pressure difference; $T_1$ is the first predetermined duration; $T_2$ is a second predetermined duration; $t_s$ is the tightening moment; $t_d$ is the current moment; k is a third modulation coefficient; || denotes an absolute value; $t_h$ is the predetermined subsequent moment.

2. The tourniquet tightening modulation system based on blood pressure measurement and vibration point sensing according to claim 1, wherein, after performing the third tightening of the tourniquet according to the second predetermined pressure further includes, when the tourniquet is unable to be tightened any further, pulling a main strap and using a toothed triple buckle to fix the tourniquet, twisting a windlass rod to increase the pressure of the tourniquet on the limb, and recording a twisting moment.

3. The tourniquet tightening modulation system based on blood pressure measurement and vibration point sensing according to claim 2, wherein, after twisting the windlass rod to increase the pressure of the tourniquet on the limb further includes, when a difference between the current moment and the twisting moment exceeds the first predetermined duration and the tourniquet is unable to be loosened, loosening the windlass rod and releasing the toothed triple buckle for a predetermined subsequent duration, then pulling the main strap again and using the toothed triple buckle to fix the tourniquet, twisting the windlass rod to increase the pressure of the tourniquet on the limb, and recording the twisting moment again.

* * * * *